US00PP31394P2

(12) United States Plant Patent
Hansen

(10) Patent No.: US PP31,394 P2
(45) Date of Patent: Jan. 21, 2020

(54) ***DELOSPERMA* PLANT NAMED 'BANANA BLAST'**

(50) Latin Name: ***Delosperma* hybrid**
Varietal Denomination: Banana Blast

(71) Applicant: Christopher M. Hansen, Zeeland, MI (US)

(72) Inventor: Christopher M. Hansen, Zeeland, MI (US)

( * ) Notice: Subject to any disclaimer, the term of this patent is extended or adjusted under 35 U.S.C. 154(b) by 0 days.

(21) Appl. No.: 16/350,513

(22) Filed: Nov. 26, 2018

(51) Int. Cl.
*A01H 5/02* (2018.01)
*A01H 6/00* (2018.01)

(52) U.S. Cl.
USPC ..... Plt./422
CPC ..... *A01H 6/00* (2018.05)

(58) Field of Classification Search
USPC ..... Plt./422
See application file for complete search history.

*Primary Examiner* — Anne Marie Grunberg
(74) *Attorney, Agent, or Firm* — Penny J. Aguirre

(57) ABSTRACT

A new cultivar of *Delosperma* plant named 'Banana Blast' that is characterized by its floriferous blooming habit, its yellow flowers with white centers, its very compact and tight mounds of foliage that do not become long or leggy during the summer growing months, its strong re-blooming habit during the entire growing season and into late fall, its small plant size, its uniform rooting habit, and its uniform blooming period with other plants in the series.

2 Drawing Sheets

Botanical classification: *Delosperma* hybrid.
Variety denomination: 'Banana Blast'.

CROSS REFERENCE TO RELATED APPLICATIONS

This application is co-pending with U.S. Plant Patent Applications filed for plants derived from the same breeding program that are entitled *Delosperma* Plant Named 'Coconut Crush' (U.S. Plant patent application Ser. No. 16/350,512), *Delosperma* Plant Named 'Fig Fusion' (U.S. Plant patent application Ser. No. 16/350,511), *Delosperma* Plant Named 'Pumpkin Perfection' (U.S. Plant patent application Ser. No. 16/350,509), *Delosperma* Plant Named 'Saucy Strawberry' (U.S. Plant patent application Ser. No. 16/350,514), and *Delosperma* Plant Named 'Tangerine Tango' (U.S. Plant patent application Ser. No. 16/350,510).

STATEMENT REGARDING PRIOR DISCLOSURES BY THE INVENTOR

The Applicant asserts that no publications or advertisements relating to sales, offers for sale, or public distribution occurred more than one year prior to the effective filing date of this application. Any information about the claimed plant less than one year prior to the effective filing date would have been obtained from a direct or indirect disclosure from the Inventor under 35 U.S.C. 102(b)(1).

BACKGROUND OF THE INVENTION

The present invention relates to a new and distinct cultivar of *Delosperma* plant of hybrid origin, botanically known as *Delosperma* 'Banana Blast' and will be referred to hereinafter by its cultivar name, 'Banana Blast'. The new cultivar of *Delosperma* is a hardy herbaceous perennial grown for use as a landscape and container plant and is particularly suitable as a groundcover.

'Banana Blast' arose from an ongoing breeding program by the Inventor in Hudsonville, Mich. The objective was to obtain a new series of *Delosperma* cultivars with more floriferous blooming habits, smaller and more compact and uniform plant habits, and blooming periods that are the same amongst all cultivars in the series when grown under the same conditions.

The Inventor made a controlled cross in July of 2014 in his test garden in Hudsonville, Mich. between an unnamed proprietary plant from the Inventor's breeding program, reference no. 275-3, as the female parent and pollen that was pooled from unnamed proprietary plants of *Delosperma* as the male parent. The exact male parent is therefore unknown. The Inventor selected 'Banana Blast' as a single unique plant in June of 2016 from the resulting seedlings.

Asexual reproduction of the new cultivar was first accomplished by stem tip cuttings in April of 2015 in Hudsonville, Mich. Asexual propagation by stem tip cuttings has determined that the characteristics are stable and reproduced true to type in successive generations.

SUMMARY OF THE INVENTION

The following traits have been repeatedly observed and are determined to be the characteristics of the new cultivar. These attributes in combination distinguish 'Banana Blast' as a unique cultivar of *Delosperma*.

1. 'Banana Blast' exhibits a floriferous blooming habit with an average of 71 flowers per plant as a 10-week-old plant grown in a 1-quart container started from a 128-cell plug.
2. 'Banana Blast' exhibits yellow flowers with white centers.
3. 'Banana Blast' exhibits very compact and tight mounds of foliage that do not become long or leggy during the summer growing months.

4. 'Banana Blast' exhibits a strong re-blooming habit during the entire growing season and into late fall.
5. 'Banana Blast' exhibits a small plant size reaching an average of 3.8 cm in height and 38 cm in width.
6. 'Banana Blast' exhibits a uniform rooting habit that occurs in just 10 days.
7. 'Banana Blast' exhibits a uniform blooming period with other plants in the series.

The seed parent plant of 'Banana Blast', no. 275-3, differs from 'Banana Blast' in having a 30% taller plant height, 65% less flowers and flowers that are lighter yellow in color. 'Banana Blast' can be most closely compared to the cultivars 'Jewel of Desert Peridot' (U.S. Plant Pat. No. 23,566) and 'WOW2011-1' (U.S. Plant Pat. No. 25,684). 'Jewel of Desert Peridot' is similar to 'Banana Blast' in having yellow flowers with white centers and a flowering period of late spring through fall. 'Jewel of Desert Peridot' differs from 'Banana Blast' in having less flowers; an average of 29 flowers per 10-week old plant, a taller plant height reaching a height of 56 cm to 71 cm, flowers that are 20% larger in size, and a less floriferous re-bloom in fall. 'WOWD2011-1' differs from 'Banana Blast' in having less flowers; an average 41 flowers per 10-week old plant, flowers that are 40% larger in size, a larger plant size reaching an average of 16 cm in height and 91 cm in width, and a much less tight and compact plant habit. 'Banana Blast' can also be compared to cultivars with co-pending patent applications from the same breeding program that have the same blooming periods. 'Coconut Crush' having U.S. patent application Ser. No. 16/350,512, differs from 'Banana Blast' in having white flowers, 'Fig Fusion' having U.S. patent application Ser. No. 16/350,511, differs from 'Banana Blast' in having hot pink flowers, 'Pumpkin Perfection' having U.S. patent application Ser. No. 16/350,509, differs from 'Banana Blast' in having orange flowers, 'Saucy Strawberry' having U.S. patent application Ser. No. 16/350,514, differs from 'Banana Blast' in having red-pink flowers, and 'Tangerine Tango' having U.S. patent application Ser. No. 16/350,510, differs from 'Banana Blast' in having red-orange flowers.

BRIEF DESCRIPTION OF THE DRAWINGS

The following is a detailed description of the new cultivar as observed on 3-month-old plants of 'Banana Blast' as grown outdoors in two-quart containers in Hudsonville, Mich.

The photograph in FIG. 1 provides a side view of 'Banana Blast' in bloom.

Figure 1:
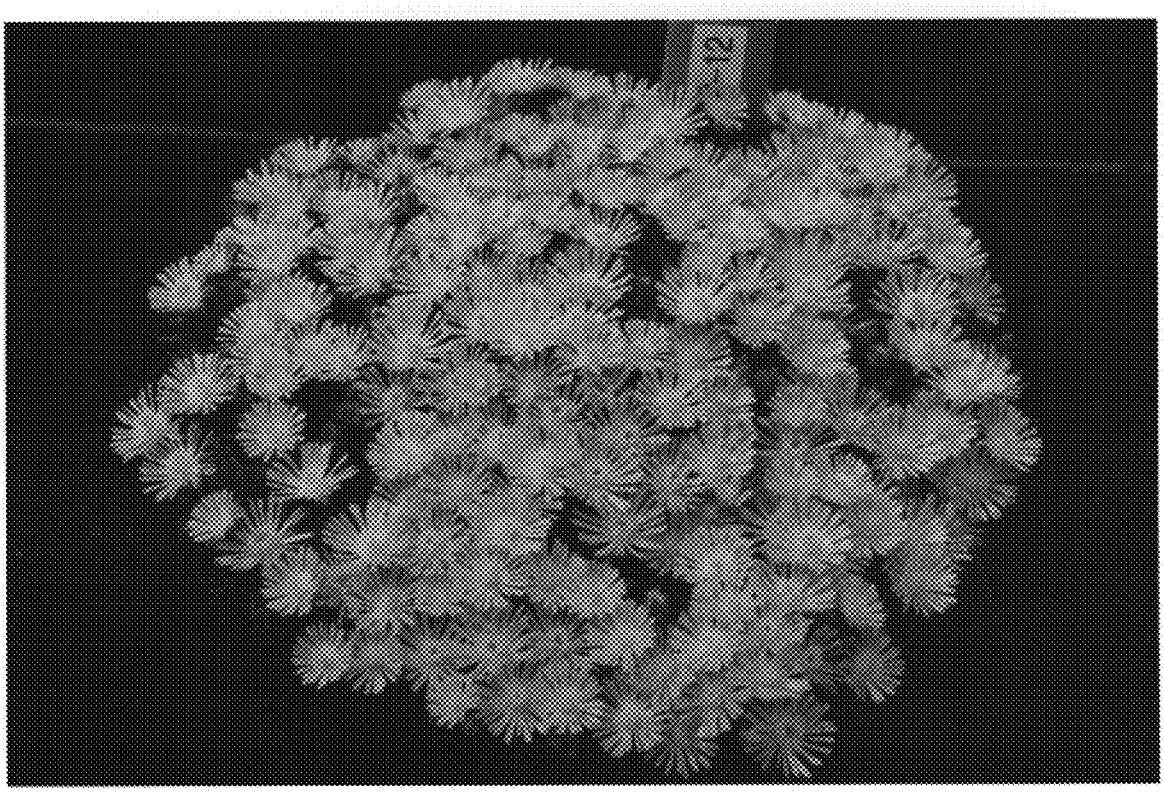
Figure 2:
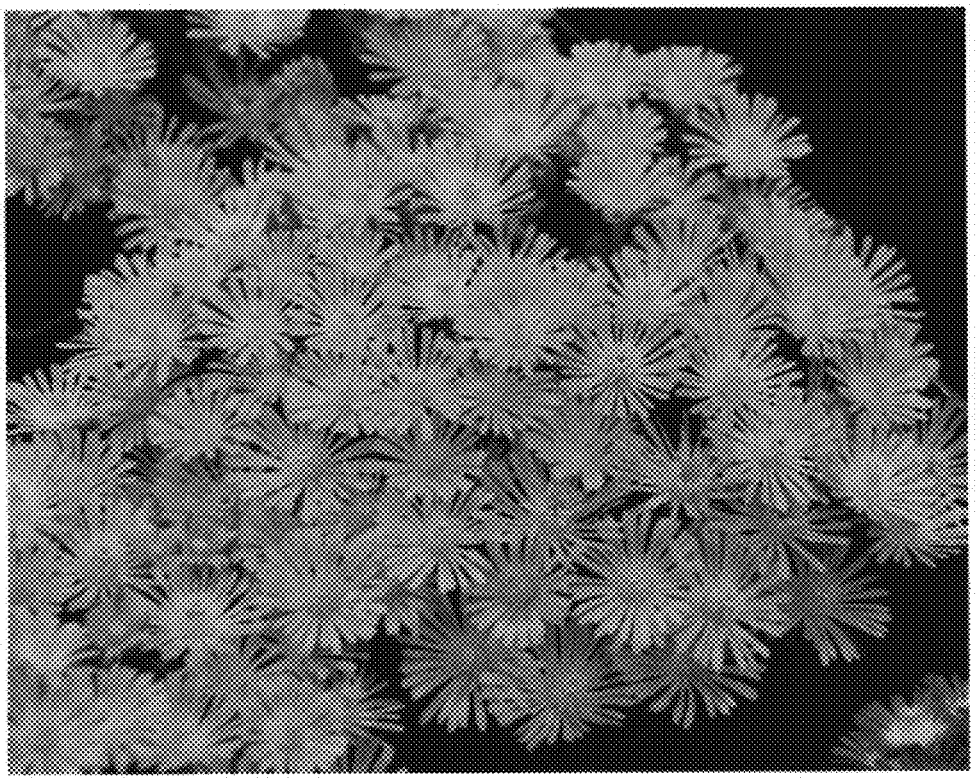

The photograph in FIG. 2 provides a close-up view of the flowers of 'Banana Blast'.

Figure 3:
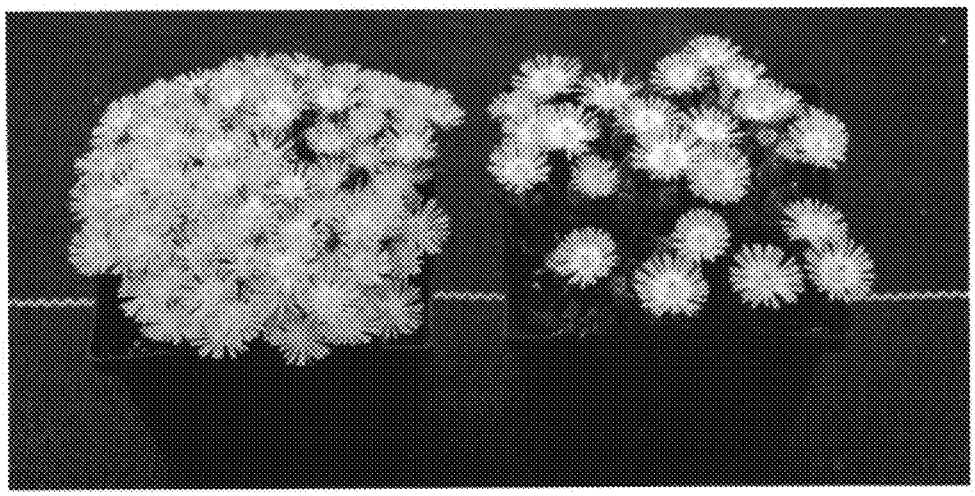

The photograph in FIG. 3 provides a comparison of 'Banana Blast' on the left and 'Jewels of Peridot' on the right.

The colors in the photograph may differ slightly from the color values cited in the detailed botanical description, which accurately describe the colors of the new *Delosperma*.

DETAILED BOTANICAL DESCRIPTION

The following is a detailed description of 3-month-old plants of the new cultivar as grown outdoors in 9-cm containers in Hudsonville, Mich. The phenotype of the new cultivar may vary with variations in environmental, climatic, and cultural conditions, as it has not been tested under all possible environmental conditions. The color determination is in accordance with The 2015 Colour Chart of The Royal Horticultural Society, London, England, except where general color terms of ordinary dictionary significance are used.

General description:

*Blooming period.*—Blooms heavily from June 1 through late July, then re-blooms through late October in Michigan.

*Plant type.*—Herbaceous perennial.

*Plant habit.*—Clumping, tightly mounded, compact ground cover.

*Height and spread.*—An average of 3.8 cm in height and about 38 cm in diameter in the landscape.

*Hardiness.*—At least in U.S.D.A. Zones 6 to 9.

*Diseases and pests.*—No susceptibility or resistance to diseases or pests has been observed.

*Root description.*—Fibrous, 199A in color.

*Root development.*—Cuttings root uniformly in 128-cell plugs in 6 weeks, 128-cell planted into a 9-cm pot or quart pot will finish and be in full bloom at 9 to 10 weeks after planting.

*Propagation.*—Stem tip cuttings.

*Growth habit.*—Moderate.

Stem description:

*Shape.*—Round.

*Stem color.*—145A.

*Stem size.*—Lateral branches; an average of 1.5 cm in length and 1 mm in diameter.

*Internode length.*—An average of 5 mm.

*Stem substance.*—Succulent.

*Stem surface.*—Young; moderately glossy and glabrous, mature is woody.

*Stem strength.*—Young; moderately strong, mature; strong.

*Branching habit.*—Freely and very densely branching, both basal and lateral, an average of 5 lateral branches per basal stem, average of 30 basal stems per plant.

Foliage description:

*Leafshape.*—Ligulate, oblong and narrow.

*Leaf substance.*—Succulent, thick.

*Leaf division.*—Simple.

*Leaf base.*—Cuneate.

*Leaf apex.*—Acute.

*Leaf venation.*—Veins are not distinguishable.

*Leaf margins.*—Entire.

*Leaf arrangement.*—Opposite to whorled.

*Leaf surface* (*upper and lower surface*).—Slightly glossy, sparsely to moderately pubescent with very short glandular hairs; too small to measure.

*Leaf color.*—Young and mature; 146A with base 142A.

*Leaf size.*—About 2.5 cm in length and 5 mm in width.

*Leaf quantity.*—Average of 30 per lateral branch.

*Leaf attachment.*—Sessile.

Inflorescence description:

*Inflorescence type.*—Flowers solitary, terminal.

*Flower number.*—Densely floriferous, quantity ranges, about 5 per basal stem.

*Flower fragrance.*—Faint, sweet and pleasant.

*Flower aspect.*—Mostly held upright.

*Flower longevity.*—A few days, self-cleaning.

*Flower type.*—Single.

*Flower size.*—Average of 1.5 cm in diameter and 5 mm in depth.

*Flower buds.*—Broadly ovate to oblong in shape, an average of 5 in diameter and 1 cm in depth, color; N144A.

*Calyx.*—Rotate in shape, average of 2 mm in depth and 4 mm in diameter.

*Sepals.*—5, rotate, narrowly ovate in shape, margin entire, an average of 5 mm in length and 2 mm in width, acute apex, cuneate base, both surfaces matte, inner and outer surface is N144A in color.

*Petals.*—An average of 25 per flower, rotate and slightly curved downward, narrowly oblanceolate in shape, surface is smooth and glossy on both surfaces, margin entire, apex acute, base cuneate, an average of 6 mm in length and 1 mm in width, color; opening and fully open flowers upper and lower surface; 9A with base NN155A.

*Petaloids.*—An average of 15 per flower, rotate and near vertical surrounding stamens, lanceolate in shape, moderately to highly glossy on both surfaces, margin entire, apex acute, base cuneate, an average of 3 mm in length and 0.5 mm in width, color upper and lower surface; 9A with base NN155A.

*Peduncle.*—Average of 3 cm in length and 2 mm in diameter, held vertical to outwards, surface dull and glaucous, color; 144A.

*Pedicel.*—None.

Reproductive organs:

*Pistils.*—5, an average of 1 mm in length, pistil, style and stigma are not distinguishable, triangular shaped, embedded in the ovary, 149A in color, ovary is 149A in color.

*Stamens.*—Average 40, anthers; dorsifixed and narrowly oblong in shape, an average of 0.5 mm in diameter, 9A in color, filaments are up to 5 mm in length NN155D in color, pollen is abundant in quantity and 9A in color.

*Fruit.*—Fruit and seed production was not observed under the conditions tested.

It is claimed:

1. A new and distinct variety of *Delosperma* plant named 'Banana Blast' as described and illustrated herein.

* * * * *